United States Patent [19]

Kinsho et al.

[11] Patent Number: 5,641,431
[45] Date of Patent: Jun. 24, 1997

[54] SILACYCLOHEXANONE COMPOUND AND A METHOD OF PREPARING A SILACYCLOHEXANE-TYPE LIQUID CRYSTAL COMPOSITION CONTAINING IT

[75] Inventors: Takeshi Kinsho; Takaaki Shimizu; Tsutomu Ogihara; Ryuichi Saito; Kazuyuki Asakura; Mutsuo Nakashima, all of Niigata-ken, Japan

[73] Assignee: Shin-Etsu Chemical Co., Ltd., Tokyo, Japan

[21] Appl. No.: 408,961

[22] Filed: Mar. 23, 1995

[30] Foreign Application Priority Data

Mar. 24, 1994 [JP] Japan .................................. 6-078125

[51] Int. Cl.$^6$ .................... C09K 19/30; C07F 7/08
[52] U.S. Cl. .................... 252/299.63; 556/406
[58] Field of Search .................... 252/299.63; 556/406

[56] References Cited

U.S. PATENT DOCUMENTS

| | | | |
|---|---|---|---|
| 4,698,177 | 10/1987 | Tanaka et al. | 252/299.63 |
| 4,820,443 | 4/1989 | Goto et al. | 252/299.63 |
| 4,822,519 | 4/1989 | Saito et al. | 252/299.61 |
| 4,853,152 | 8/1989 | Goto et al. | 252/299.63 |
| 5,454,977 | 10/1995 | Shimizu et al. | 252/299.61 |
| 5,468,421 | 11/1995 | Matsui et al. | 252/299.63 |

FOREIGN PATENT DOCUMENTS 0632044  6/1994  European Pat. Off. .

OTHER PUBLICATIONS

Journal of Organometallic Chemistry, vol. 133, pp. 7–17, Nov. 30, 1976; "Acetolysis of 4,4–Disubstituted 4–Silacyclohexyl Tosylates: Effect Of Remote Silicon Substitution On Organic Reactivity"; S. Washburne, et al.

Primary Examiner—Shean C. Wu
Attorney, Agent, or Firm—Townsend & Banta

[57] ABSTRACT

A silacyclohexanone compound represented by the following general formula (I).

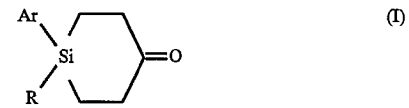

wherein Ar denotes a phenyl group or a tolyl group. R denotes a tolyl group, a linear-chain alkyl group with a carbon number of 2–10, a mono- or di-fluoroalkyl group with a carbon number of 1–10, a branched-chain alkyl group with a carbon number of 3–8 or an alkoxyalkyl group with a carbon number of 2–7. Also, a method of manufacturing silacyclohexane-type liquid crystal compounds represented by the general formula (II)

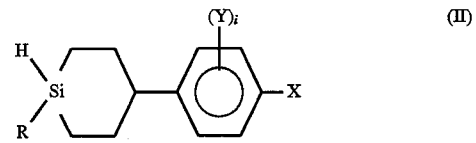

and the general formula (III)

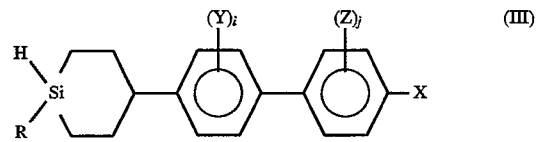

which are derived from this compound.

4 Claims, No Drawings

SILACYCLOHEXANONE COMPOUND AND A METHOD OF PREPARING A SILACYCLOHEXANE-TYPE LIQUID CRYSTAL COMPOSITION CONTAINING IT

BACKGROUND OF THE INVENTION

1. Field of the Invention

This invention relates to a silacyclohexanone compound and a method of preparing a silacyclohexane-type liquid crystal compound using it.

2. The Prior Art

A liquid crystal display element utilizes the optical anisotropy and dielectric anisotropy of liquid crystal substances. Display methods include the TN mode (twisted nematic mode), the STN mode (super twisted nematic mode), the SBE mode (super birefringence mode), the DS mode (dynamic scattering mode), the guest-host mode, the PAP mode ("deformation of aligned phase" mode), the PD mode (polymer dispersion mode) and the OMI mode (optical mode interference mode). The most common display device has a twisted nematic structure based on the Schadt-Helfrich mode.

The properties required of the liquid crystal substance used in these liquid crystal displays are somewhat different depending on the display method. However, a wide liquid crystal temperature range and stability with regard to moisture, air, light, heat, electric fields, etc., are properties commonly required in all display methods. Furthermore, it is desirable for the liquid crystal material to have a low viscosity, and also to have a short address time, low threshold voltage and high contrast in the cell(s).

In recent years, along with the expansion of the applications of liquid crystal displays, the characteristics required of liquid crystal materials are becoming more and more advanced and demanding. In particular, superior characteristics such as improved low temperature performance, a wider temperature range for automobile onboard use and a lower driving voltage, compared with conventional liquid crystal substances, are desired.

BRIEF SUMMARY OF THE INVENTION

From such a viewpoint, the inventors developed, for the purpose of improving the characteristics of liquid crystal substances, new silacyclohexane-type liquid crystal compounds containing silicon atoms in their molecules and filed a patent application(s) for these compounds. The object of this invention is to provide a silacyclohexanone compound which is a useful intermediate when preparing these silacyclohexane-type liquid crystal compounds, as well as a method of preparing the silacyclohexane-type liquid crystal compounds derived from it.

This invention provides a useful intermediate for preparing a silacyclohexane-type liquid crystal compound represented by the following general formula (II)

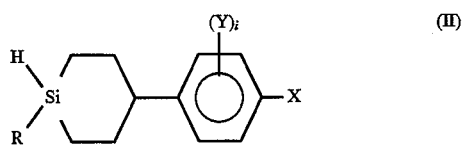

(in this formula, R denotes a phenyl group, a tolyl group, a linear-chain alkyl group with a carbon number of 1–10, a mono- or di-fluoroalkyl group with a carbon number of 1–10, a branched-chain alkyl group with a carbon number of 3–8, or an alkoxyalkyl group with a carbon number of 2–7; X denotes a CN, F, Cl, Br, $CF_3$, $OCF_3$, $OCHF_2$, $OCHFCl$, $OCF_2Cl$, $CF_2Cl$, $OCH_2CF_2H$, R or OR group; Y denotes a halogen or $CH_3$; and i denotes an integer 0–2) as well as a silacyclohexane-type compound represented by the following general formula (III)

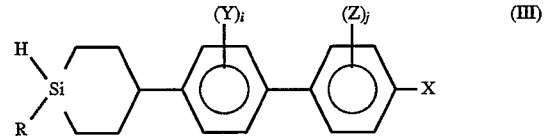

(in this formula, Z denotes a halogen or $CH_3$, and j denotes an integer 0–2), wherein said intermediate is a silacyclohexanone compound represented by the following general formula (I).

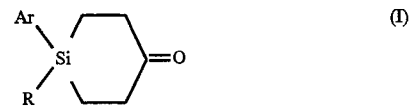

(In this formula, Ar denotes a phenyl group or a tolyl group. R denotes At, a linear-chain alkyl group with a carbon number of 1–10, a mono- or di-fluoroalkyl group with a carbon number of 1–10, a branched-chain alkyl group with a carbon number of 3–8 or an alkoxyalkyl group with a carbon number of 2–7).

This invention also provides a method of preparing a silacyclohexane-type liquid crystal compound characterized by reacting the compound as represented by said general formula (I) with an organometallic reagent represented by the following general formula

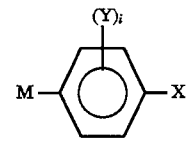

(in this formula, M denotes MgP (P denotes a halogen atom), ZnP or Li; X denotes a CN, F, Cl, Br, $CF_3$, $OCF_3$, $OCHF_2$, OCHFCl, $OCF_2Cl$, $CF_2Cl$, $OCH_2CF_2H$, R or OR group; Y denotes a halogen or $CH_3$; and i denotes an integer 0–2) to obtain a compound represented by the following general formula

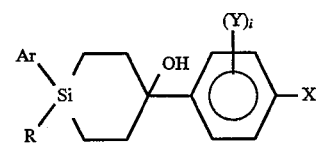

then conducting hydrogenolysis or dehydration followed by hydrogenation to obtain a compound represented by the following general formula

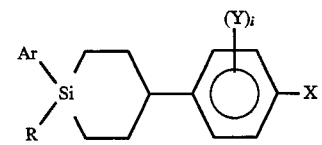

and finally conducting desilylation followed by reduction to obtain a silacyclohexane-type liquid crystal compound represented by the following general formula (II)

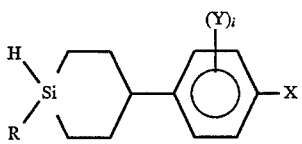
(II)

This invention also provides a method of preparing a silacyclohexane-type liquid crystal compound characterized by reacting the compound as represented by said general formula (I) with an organometallic reagent represented by the following general formula

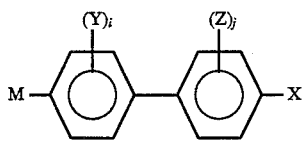

(in this formula, M denotes MgP (P denotes a halogen atom), ZnP or Li; X denotes a CN, F, Cl, Br, $CF_3$, $OCF_3$, $OCHF_2$, OCHFCl, $OCF_2Cl$, $CF_2Cl$, $OCH_2CF_2H$, R or OR group; Y and Z denote a halogen or $CH_3$; i and j both denote integers 0–2) to obtain a compound represented by the following general formula

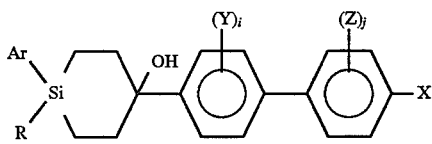

then conducting hydrogenolysis or dehydration followed by hydrogenation to obtain a compound represented by the following general formula

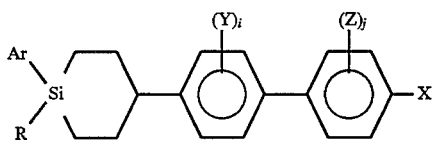

and finally conducting desilylation followed by reduction to obtain a silacyclohexane-type liquid crystal compound represented by the following general formula (III)

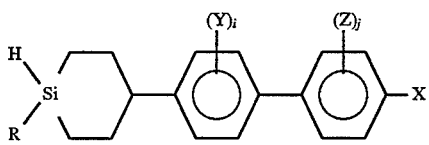
(III)

This invention also provides a method of preparing a silacyclohexane-type liquid crystal compound characterized by reacting the compound as represented by said general formula (I) with an organometallic reagent represented by the following general formula

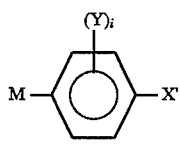

(in this formula, M denotes MgP (P denotes a halogen atom), ZnP or Li; X' denotes a halogen; Y denotes a halogen or $CH_3$; i denotes an integer 0–2) to obtain a compound represented by the following general formula

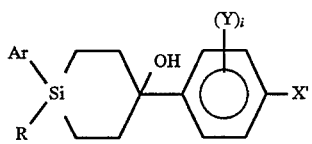

then conducting hydrogenolysis or dehydration followed by hydrogenation to obtain a compound represented by the following general formula

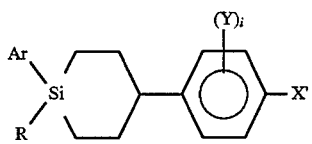

then reacting this compound with an organometallic reagent represented by the following general formula

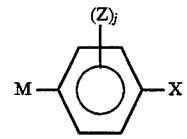

(X denotes a CN, F, Cl, Br, $CF_3$, $OCF_3$, $OCHF_2$, OCHFCl, $OCF_2Cl$, $OCH_2CF_2H$, R or OR group; Z denotes a halogen or $CH_3$; j denotes an integer 0–2) in the presence of a transition metal catalyst to obtain a compound represented by the following general formula

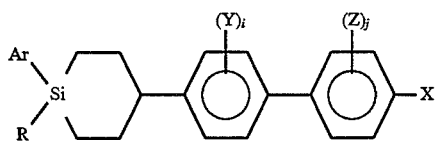

and finally conducting desilylation followed by reduction to obtain a silacyclohexane-type liquid crystal compound represented by the following general formula (III)

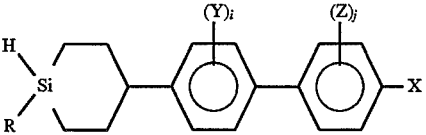
(III)

DETAILED DESCRIPTION

This invention is further described in detail below. The silacyclohexanone compound of this invention represented by the following general formula (I)

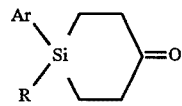
(I)

(in this formula, Ar denotes a phenyl group or a tolyl group and R denotes Ar, a linear-chain alkyl group with a carbon number of 1–10, a mono- or di-fluoroalkyl group with a carbon number of 1–10, a branched-chain alkyl group with a carbon number of 3–8 or an alkoxyalkyl group with a carbon number of 2–7) can be prepared by either of the two methods described below.

The first method has the following synthesis path:

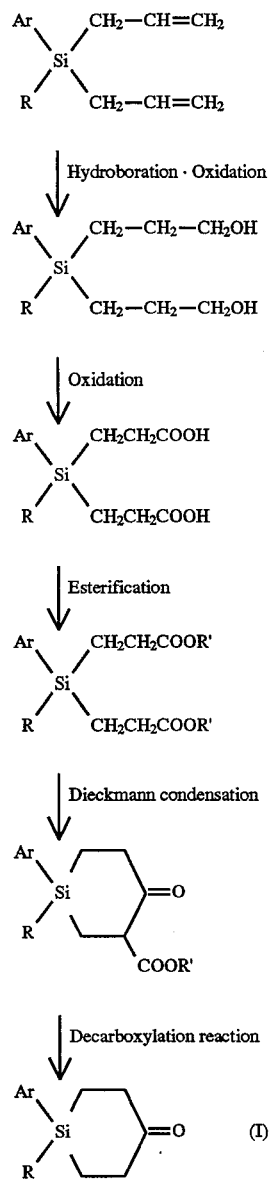

The second method has the following synthesis path:

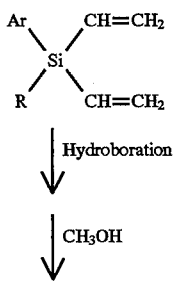

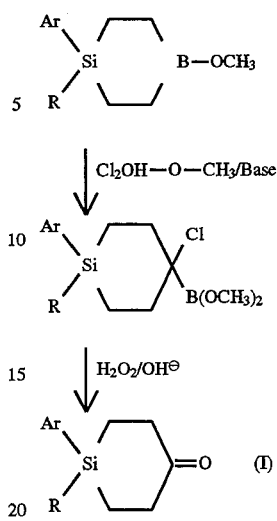

The silacyclohexanone compound obtained as described above is used to prepare various silacyclohexane-type liquid crystal compounds.

A method of deriving the silacyclohexane-type compound from the obtained silacyclohexanone compound is described below.

As shown below, an alcohol compound is obtained by reacting an organometallic reagent which can be prepared easily from the corresponding halide with the silacyclohexanone compound described above.

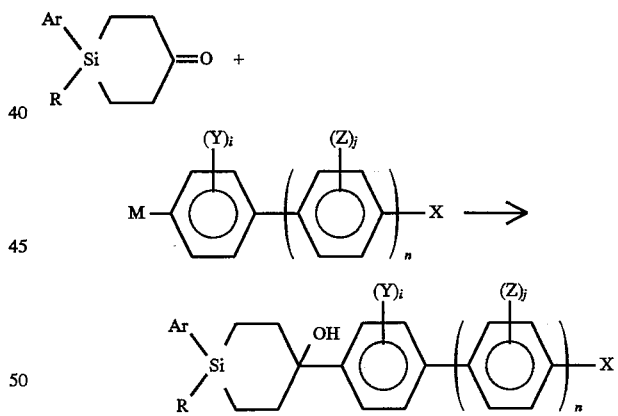

(In this formula, n denotes 0 or 1.)

Examples of the organometallic reagent are Grignard reagents, organozinc reagents and organolithium reagents, with any of which the reaction proceeds with a high yield.

Hydrogenolysis or a dehydration reaction using an acid catalyst followed by hydrogenation on the generated double bond is conducted on the obtained alcohol compound to obtain the silacyclohexane compound.

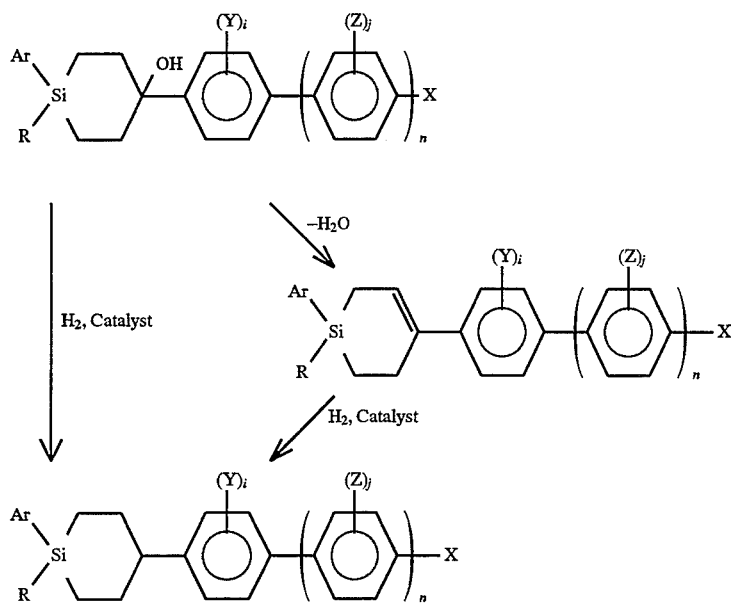

Examples of the catalyst used in hydrogenolysis and hydrogenation are metals such as palladium, platinum, rhodium, nickel and ruthenium. In particular, palladium-carbon, palladium-barium sulfate, palladium-silious earth, platinum oxide, platinum-carbon, rhodium-carbon, Raney nickel, etc. give good results.

Examples of the acid used in the dehydration reaction are inorganic acids such as hydrochloric acid, sulfuric acid and nitric acid as well as their salts, and organic acids such as p-toluenesulfonic acid, camphorsulfonic acid and trifluoroacetic acid. For the rapid removal of generated water, azeotropy can be utilized to accelerate the reaction by using a hydrocarbon such as benzene, toluene, xylene, cumene, hexane or isooctane as a solvent.

The desilylation reaction using an electrophilic reagent is then conducted to obtain a halosilacyclohexane compound, followed by a reduction reaction.

Examples of the electrophilic reagent are halogens, hydrogen halides, metal halides, sulfonic acid derivatives, acid halides, alkyl halides, etc. Particularly preferable are iodine, bromine, chlorine, iodine monochloride, hydrogen chloride, hydrogen bromide, hydrogen iodide, mercury (II) chloride, trimethylsilyl chlorosulfonic acid, acetyl chloride, acetyl bromide, benzoyl chloride, t-butyl chloride, etc. In order to increase the reaction rate, the addition of Lewis acids such as aluminum chloride, zinc chloride, titanium tetrachloride and boron trifluoride and/or light irradiation can be conducted.

Examples of the reagent used to reduce the halosilacyclohexane compound thus obtained are metal hydrides such as sodium hydride, calcium hydride, trialkylsilanes, boranes, dialkyl aluminum, etc., complex hydrides such as lithium aluminum hydride, sodium borohydride, lithium borohydride, potassium borohydride, tributyl ammonium

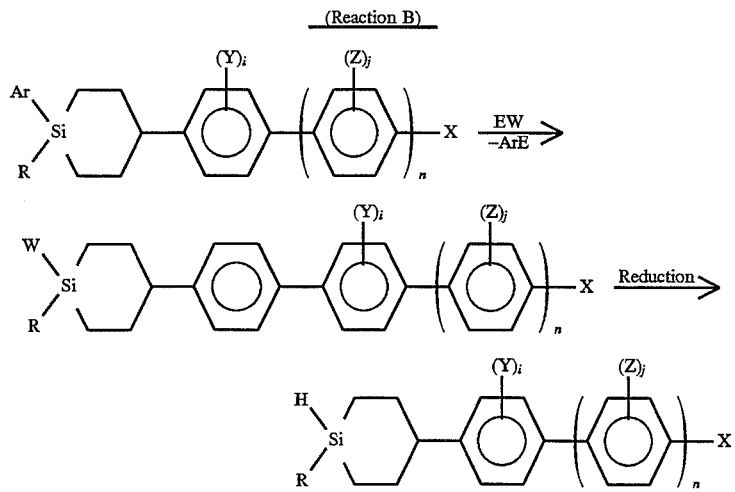

(In this formula, EW denotes the electrophilic reagent, and W denotes a halogen.)

borohydride, etc. and substituted hydride compounds derived from them such as lithium trialkoxy aluminum hydride, sodium di (methoxyethoxy) aluminum hydride, lithium triethyl borohydride, sodium cyanoborohydride, etc.

Using the methods described above, synthesis of the silacyclohexane-type liquid crystal compound became possible.

Of the products obtained by the reaction shown in the reaction A, the compound represented by the general formula

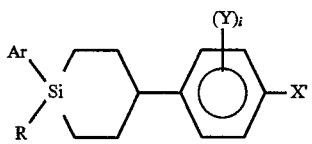

(X' denotes a halogen atom) which corresponds to n=0 can be used to derive the compound represented by the general formula

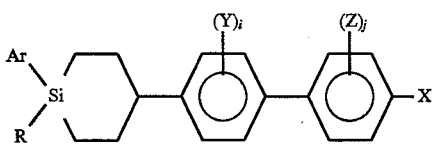

which corresponds to n=1. The reaction formula is shown below.

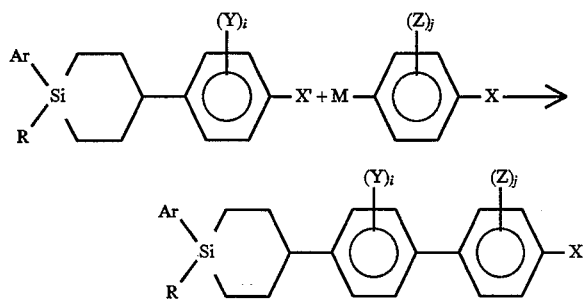

This reaction is carried out in the presence of a transition metal catalyst. Palladium compounds and nickel compounds are particularly preferable for the catalyst.

Examples of the palladium catalysts are zero-valent palladium compounds such as tetrakis (triphenylphosphine) palladium (0) and di[1,2-bis (diphenylphosphino)ethane] palladium(0), and compounds composed of a divalent palladium compound such as palladium acetate and palladium chloride and a ligand(s), as well as a combination of these and a reducing agent.

Examples of the nickel catalysts are divalent nickel compounds such as 1,3-bis(diphenylphosphino)propane nickel (II) chloride, 1,2-bis(diphenylphosphino)ethane nickel (II) chloride and bis(triphenylphosphine)nickel (II) chloride, and zero-valent nickel compounds such as tetrakis (triphenylphosphine) nickel(0).

The compound obtained by the reaction shown in the reaction C can be used in the reaction shown in the reaction B to derive a silacyclohexane-type liquid crystal compound.

The compound thus obtained can be purified using a conventional method such as recrystallization and chromatography to obtain the target product, i.e. the trans isomer of the silacyclohexane-type liquid crystal compound.

EXAMPLE

The details of this invention are described below by referring to specific examples.

Example 1

Preparation of di(2-ethoxycarbonylethyl)phenyl-n-pentylsilane 50 g of boron trifluoride ether complex was dripped into a mixed solution of 100 g of diallylphenyl-n-pentylsilane, 9.6 g of sodium borohydride and 500 g of tetrahydrofuran. After the reaction mixture was stirred for 4 hours at room temperature, a 300 ml aqueous solution of 20% sodium hydroxide and then a 100 ml aqueous solution of 30% hydrogen peroxide were dripped into the mixture. After an overnight stirring were dripped into the mixture. After an overnight stirring at room temperature, extraction was conducted using ethyl acetate. Following conventional washing and concentration procedures, 120 g of di(3-hydroxypropyl)phenyl-n-pentylsilane was obtained. IR (liquid film) νmax: 3030 (s, br), 2920 (s), 2870 (s), 1420 (m), 1105 (s), 1050 (s), 1005 (s) and 850 (m) cm$^{-1}$ This crude product was added to a mixture of 100 g of potassium permanganate and a 800 ml aqueous solution of 20% sodium hydroxide, followed by 12 hours of stirring at room temperature. Dilute hydrochloric acid was added to the reaction mixture to make it acidic, and extraction was conducted using methylene chloride. Following conventional washing and concentration procedures, 125 g of di(2-carboxyethyl)phenyl-n-pentylsilane was obtained.

IR (liquid film) νmax: 3500–2800 (s, br), 2920 (s), 1710 (m), 1425 (s), 1240 (s), 1200 (s), 1115 (s) and 905 (m) cm$^{-1}$ 500 ml of benzene, 60 ml of ethanol and 1 g of p-toluenesulfonic acid were added to this crude product and heated refluxing was conducted while the water generated was removed. When the generation of water was completed, ice water was added and extraction was conducted using methylene chloride. After conventional washing and concentration procedures, purification was conducted by means of silica-gel chromatography to obtain 107 g of the target product (yield 70% from diallylphenyl-n-pentylsilane).

$^1$H-NMR (100 MHz, CDCl$_3$): δ0.70–1.00 (5H, m), 1.00–1.44 (16H, m), 2.12–2.45 (4H, m), 4.08 (4H, q), 7.20–7.66 (5H, m) ppm IR (liquid film) νmax: 2920 (s), 1735 (s), 1425 (m), 1205 (s), 1110 (s) and 1045 (s) cm$^{-1}$ The following compounds were obtained in the same manner as Example 1.

Example 2

Di(2-ethoxycarbonylethyl)diphenylsilane $^1$H-NMR (100 MHz, CDCl$_3$): δ1.20 (6H, t), 1.25–1.55 (4H, m), 2.18–2.44 (4H, m), 4.06 (4H, q), 7.30–7.60 (10H, m) ppm IR (liquid film) νmax: 2920 (s), 1725 (s), 1430 (s), 1375 (s), 1345 (s), 1210 (s), 1110 (s), 1050 (s) and 920 (m) cm$^{-1}$

Example 3

Di(2-ethoxycarbonylethyl)phenyl-n-propylsilane $^1$H-NMR (100 MHz, CDCl$_3$): δ0.70–1.60 (17H, m), 2.10–2.40 (4H, m), 4.10 (4H, q), 7.20–7.60 (5H, m) ppm IR (liquid film) νmax: 2960 (s), 1735 (s), 1425 (m), 1365 (m), 1205 (s), 1110 (s) and 1050 (s) cm$^{-1}$

Example 4

Di(2-ethoxycarbonylethyl)-n-pentyl-p-tolylsilane $^1$H-NMR (100 MHz, CDCl$_3$): δ0.65–1.00 (5H, m), 1.00–1.46 (16H, m), 2.14–2.40 (4t m), 2.85 (3H, s), 4.09 (4H, q), 7.10–7.45 (4H, m) ppm IR (liquid film) vmax: 2915 (s), 1725 (s), 1430 (m), 1370 (s), 1210 (s), 1105 (s), 1040 (s) and 925 (m) cm$^{-1}$ Example 5

Di(2-ethoxycarbonylethyl)-n-propyl-p-tolylsilane $^1$H-NMR (100 MHz, CDCl$_3$): δ0.70–1.60 (17H, m), 2.15–2.42 (7H, m), 4.09 (4H, q), 7.10–7.46 (4H, m) ppm IR (liquid film) vmax: 2930 (s), 1735 (s), 1425 (m), 1205 (s), 1370 (m), 1210 (s), 1105 (s) and 1050 (s) cm$^{-1}$ Example 6

Di (2-ethoxycarbonylethyl)ethyl-p-tolylsilane $^1$H-NMR (100 MHz, CDCl$_3$): δ0.70–1.50 (15H, m), 2.10–2.40 (7H, m), 4.10 (4H, q), 7.10–7.48 (4H, m) ppm IR (liquid film) vmax: 2925 (s), 1730 (s), 1425 (m), 1375 (m), 1210 (s), 1110 (s) and 1050 (s) cm$^{-1}$ Example 7

Preparation of 4-n-pentyl-4-phenyl-4-silacyclohexanone 194 g of di(2-ethoxycarbonylethyl)phenyl-n-pentylsilane was added to a suspension of 18.5 g sodium hydride and 800 ml of toluene, and the mixture was stirred for 3 hours at 100° C. while ethanol was distilled away. After cooling, 500 ml of 20% hydrochloric acid was added to the reaction mixture to make it neutral, and then the toluene layer was concentrated to obtain 150 g of 2-ethoxycarbonyl-4-n-pentyl-4-phenyl-4-silacyclohexanone.

IR (liquid film) vmax: 2925 (s), 1735 (s), 1705 (s), 1425 (m), 1220 (s), 1155 (m), 1110 (s), 1060 (s), 725 (s) and 695 (s) cm$^{-1}$ 40 g of table salt, 12 g of water and 700 ml of dimethylsulfoxide was added to this crude product and refluxing was conducted for 15 hours. After cooling the reaction mixture, water was added and extraction was conducted using methylene chloride. After conventional washing and concentration procedures, the extract was purified by means of silica-gel chromatography to obtain 115 g of the target product (yield 86%).

$^1$H-NMR (100 MHz, CDCl$_3$): δ0.70–1.00 (5H, m), 1.00–1.60 (10H, m), 2.56 (4H, t), 7.10–7.65 (5H, m) ppm IR (liquid film) vmax: 2925 (s), 1705 (s), 1425 (m), 1310 (m), 1155 (m), 1110 (s), 1080 (s), 725 (s) and 700 (s) cm$^{-1}$ The following compounds were obtained in the same manner as Example 7.

Example 8

4,4-diphenyl-4-silacyclohexanone $^1$H-NMR (100 MHz, CDCl$_3$): δ1.40–1.66 (4H, m), 2.54–2.80 (4H, m), 7.25–7.70 (10H, m) ppm IR (KBr disc) vmax: 2945 (m), 1695 (s), 1425 (s), 1165 (m), 1110 (s), 955 (m), 730 (s) and 710 (s) cm$^{-1}$ Example 9

4-n-propyl-4-phenyl-4-silacyclohexanone $^1$H-NMR (100 MHz, CDCl$_3$): δ0.70–1.06 (5H, m), 1.06–1.60 (6H, m), 2.56 (4H, t), 7.25–7.66 (5H, m) ppm IR (liquid film) vmax: 2925 (s), 1705 (s), 1425 (m), 1310 (m), 1155 (m), 1110 (s), 1085 (m), 1065 (m), 730 (s) and 700 (s) cm$^{-1}$ Example 10

4-n-pentyl-4-p-tolyl-4-silacyclohexanone $^1$H-NMR (100 MHz, CDCl$_3$): δ0.70–1.00 (5H, m), 1.00–1.65 (10H, m), 2.36 (3H, s), 2.56 (4H, t), 7.15–7.55 (4H, m) ppm IR (liquid film) vmax: 2920 (s), 1705 (s), 1415 (m), 1315 (m), 1265 (m), 1160 (m), 1110 (s), 1080 (s), 955 (m) and 800 (s) cm$^{-1}$ Example 11

Preparation of 4-n-pentyl-4-phenyl-4-silacyclohexanone

A mixture of 15.9 g of 9-borabicyclo [3.3.1] nonan, 14.8 g of n-pentylphenyldivinylsilane and 150 ml of n-hexane was refluxed for 2 hours and then cooled with ice water. 7.0 ml of borane-dimethylsufide was added to the mixture, which was then heated again and refluxed for 2 hours. After cooling, 16 ml of methanol was added at room temperature and the mixture was stirred for 2 hours at 0° C. 25.0 g of dichloromethylmethyl ether was then dripped into the mixture, followed by also dripping a hexane-tetrahydrofuran (1:1) solution of 1.33M lithium t-butoxide into the mixture. After stirring at room temperature for 2 hours, 80 ml of ethanol, 10 ml of water and 10.0 g of sodium hydroxide were added. Then 80 ml of an aqueous solution of 30% hydrogen peroxide was slowly added. After stirring at room temperature for 2 hours, the organic layer was dried/concentrated to obtain a mixture of the target product and bicyclo [3.3.1] nonan-9-one. They were separated by means of silica-gel chromatography to obtain 15.2 g (yield 91%) of the target product. The target product thus obtained exhibited the same spectra as those of Example 7.

The following compounds were obtained in the same manner as Example 11.

Example 12

4-n-propyl-4-p-tolyl-4-silacyclohexanone $^1$H-NMR (100 MHz, CDCl$_3$): δ0.70–1.05 (5H, m), 1.05–1.60 (6H, m), 2.37 (3H, s), 2.56 (4H, t), 7.12–7.66 (4H, m) ppm IR (liquid film) vmax: 2940 (s), 1710 (s), 1415 (m), 1315 (m), 1265 (m), 1155 (s) and 1110 (s) cm$^{-1}$ Example 13

4-ethyl-4-p-tolyl-4-silacyclohexanone $^1$H-NMR (100 MHz, CDCl$_3$): δ0.70–1.50 (9H, m) 2.38 (3H, t), 2.56 (4H, t), 7.10–7.58 (4H, m) ppm IR (liquid film) vmax: 2925 (s), 1705 (s), 1415 (m), 1310 (m), 1160 (m), 1115 (s), 800 (m), 755 (s), 725 (s) and 700 (s) cm$^{-1}$ Example 14

Preparation of trans-4-(4-chlorophenyl)-1-n-propyl-1-silacyclohexane 10.0 g of 4-n-propyl-4-phenyl-4-silacyclohexanone was dripped into a 50 ml tetrahydrofuran solution of 1.0M p-chlorophenyl magnesium chloride at 40°–50° C. After stirring for 2 hours at 50° C., the mixture was poured into a saturated aqueous solution of ammonium chloride and extraction was conducted using benzene. 500 mg of p-toluenesulfonic acid monohydrate was then added to the benzene solution and refluxing was conducted while the water generated was distilled away. After the water stopped distilling away, the benzene layer was washed with an aqueous solution of sodium bicarbonate, dried and concentrated to obtain 4-(4-chlorophenyl)-1-phenyl-1-n-propyl-1-silacyclohex-3-ene. This was then dissolved in 50 ml of ethanol and hydrogenation was conducted using 1.0 g of palladium carbon as a catalyst. After the catalyst was filtered out, the product was concentrated to obtain 14.0 g of 4-(4-chlorophenyl)-1-phenyl-1-n-propyl-1-silacyclohexane.

IR (KBr disc) vmax: 2920 (s), 1490 (s), 1480 (s), 1425 (m), 1110 (m), 1090 (m), 875 (s), 740 (s) and 700 (s) cm$^{-1}$ A 50 ml carbon tetrachloride solution of 1.0M iodine monochloride was added to this and the mixture was stirred for 30 minutes, followed by concentration. The residue was dissolved in 10 ml of tetrahydrofuran and then dripped into a mixture of 2.0 g of lithium aluminum hydride and 30 ml of tetrahydrofuran at 0° C. The reaction mixture was stirred for 1 hour and then poured into 100 ml of 5% hydrochloric acid, followed by extraction using ethyl acetate. After conventional washing, drying and concentration procedures, purification was conducted by means of silica-gel chromatography to obtain 8.10 g (yield 74%) of the target product.

$^1$H-NMR (100 MHz, CDCl$_3$): δ0.40–0.75 (4H, m), 0.75–1.16 (5H, m), 1.18–1.85 (4H, m), 1.85–2.25 (2H, m), 2.36 (1H, tt), 3.70–3.96 (1H, m), 7.00–7.32 (4H, m) ppm IR (liquid film) vmax: 2920 (s), 2100 (s), 1490 (s), 1400 (m), 1090 (s), 985 (s), 890 (s), 880 (s) and 815 (s) cm$^{-1}$ The following compounds were obtained in the same manner as Example 14.

Example 15

Trans-4-(4-chlorophenyl)-1 -n-pentyl-1 -silacyclohexane $^1$H-NMR (100 MHz, CDCl$_3$): δ0.40–1.02 (7H, m), 1.02–1.64 (8H, m), 1.64–1.90 (2H, m), 1.90–2.20 (2H, m), 2.36 (1H, tt), 3.70–3.96 (1H, m), 7.00–7.35 (4H, m) ppm IR (liquid film) vmax: 2920 (s), 2110 (s), 1495 (s), 1465 (m), 1415 (m), 1095 (s), 990 (m), 880 (s) and 815 (s) cm$^{-1}$

Example 16

Trans-4-(4-chlorophenyl)-1-n-hexyl- 1-silacyclohexane $^1$H-NMR (100 MHz, CDCl$_3$): δ0.40–1.02 (7H, m), 1.02–1.62 (10H, m), 1.62–1.88 (2H, m), 1.88–2.22 (2H, m), 2.36 (1H, tt), 3.70–8.96 (1H, m), 7.00–7.35 (4H, m) ppm IR (liquid film) vmax: 2920 (s), 2100 (s), 1495 (s), 1460 (m), 1410 (m), 1180 (m), 1095 (s), 985 (m), 880 (s) and 805 (s) cm$^{-1}$

Example 17

Trans-4- (4-chlorophenyl)-1-n-heptyl-1-silacyclohexane $^1$H-NMR (100 MHz, CDCl$_3$): δ0.40–1.06 (7H, m), 1.06–1.66 (12H, m), 1.66–1.92 (2H, m), 1.92–2.20 (2H, m), 3.70–3.96 (1H, m), 7.00–7.35 (4H, m) ppm GC-MS (70 eV) (m/z)$^+$: 127, 154, 209, 252, 280 and 308

Example 18

Trans-4-(4-chlorophenyl)-1-n-octyl-1-silacyclohexane $^1$H-NMR (100 MHz, CDCl$_3$): δ0.40–1.06 (7H, m), 1.06–1.64 (14H, m), 1.64–1.90 (2H, m), 1.90–2.18 (2H, m), 2.88 (1H, tt), 3.72–3.96 (1H, m), 7.00–7.32 (4H, m) ppm IR (KBr disc) vmax: 2920 (s), 2100 (s), 1495 (m), 1460 (m), 1410 (m), 1090 (m), 985 (s), 880 (s) and 805 (s) cm$^{-1}$

Example 19

Trans-4-(4-chlorophenyl)-1-n-nonyl-1-silacyclohexane $^1$H-NMR (100 MHz, CDCl$_3$): δ0.40–1.04 (7H, m), 1.04–1.64 (16H, m), 1.64–1.88 (2H, m), 1.88–2.20 (2H, m), 2.87 (1H, tt), 2.87 (1H, tt), 3.70–3.95 (1H, m), 7.00–7.30 (4H, m) ppm IR (liquid film) vmax: 2925 (s), 2100 (s), 1495 (m), 1460 (m), 1410 (m), 1095 (s), 990 (s), 880 (s) and 815 (s) cm$^{-1}$

Example 20

Trans-4-(4-fluorophenyl)-1-n-pentyl-1-silacyclohexane $^1$H-NMR (270MHz, CDCl$_3$): δ0.56–0.74 (4H, m), 0.90 (3H, t), 1.04 (2H, d), 1.34 (6H, m), 1.64 (2H, ddd), 2.06–2.13 (2H, m), 2.38 (1H, tt), 3.81–3.85 (1H, m), 6.90–7.00 (2H, m), 7.08–7.26 (2H, m) ppm IR (liquid film) vmax: 2920 (s), 2100 (s), 1510 (s), 1458 (m), 1408 (m), 1228 (s), 987 (s), 887 (s) and 825 (s) cm$^{-1}$

Example 21

Trans -4-(4 -fluorophenyl)-1-n-hexyl-1-silacyclohexane

13C-NMR (67.5 MHz, CDCl$_3$): δ10.55 (s), 12.11 (s), 14.12 (s), 22.58 (s), 24.36 (s), 31.59 (s), 32.83 (s), 33.43 (s), 114.90 (d), 127.91 (d), 144.35 (d) and 161.06 (d) ppm IR (liquid film) vmax: 2920 (s), 2100 (s), 1510 (s), 1458 (m), 1408 (m), 1228 (s), 1159 (m), 987 (s), 887 (s) and 816 (s) cm$^{-1}$

Example 22

Trans4-(4-fluorophenyl)-1-n-heptyl-1-silacyclohexane $^{13}$C-NMR (67.5 MHz, CDCl$_3$): δ10.56 (s), 12.13 (s), 14.11 (s), 22.74 (s), 24.44 (s), 29.08 (s), 31.85 (s), 33–19 (s), 33.45 (s), 46.92 (s), 114.90 (d), 127.89 (d), 144.31 (d) and 161.09 (d) ppm IR (liquid film) vmax: 2920 (s), 2100 (s), 1510 (s), 1458 (m), 1408 (m), 1228 (s), 985 (s), 88? (s) and 820 (s) cm$^{-1}$

Example 23

Trans-4-(3,4-difluorophenyl)-1-n-heptyl-1-silacyclohexane $^{13}$C-NMR (67.5 MHz, CDCl$_3$): δ10.42 (s), 12.03 (s), 14.09 (s), 22.70 (s), 24.3? (s), 29.02 (s), 31.80 (s), 33.11 (s), 33.27 (s), 46.85 (d), 115.33 (d), 116.78 (d), 122.37 (dd), 145.67 (dd), 147.49 (dd) and 151.12 (dd) ppm IR (liquid film) vmax: 2920 (s), 2102 (s), 1517 (s), 1431 (m), 1407 (m), 1284 (s), 1213 (s), 1114 (s), 987 (s), 960 (s), 889 (s) and 811 (s) cm$^{-1}$

Example 24

Trans -4-(4-cyanophenyl)-1-n-pentyl-1-silacyclohexane $^1$H-NMR (100 MHz, CDCl$_3$): δ0.40–1.06 (7H, m), 1.06–1.67 (8H, m), 1.67–1.92 (2H, m), 1.92–2.26 (2H, m), 2.46 (1H, tt), 3.70–3.98 (1H, m), 7.16–7.38 (2H, m), 7.50–7.68 (2H, m) ppm IR (liquid film) vmax: 2920 (s), 2227 (s), 2104 (s), 1608 (m), 1502 (m), 1458 (m), 1408 (m), 987 (s), 881 (s) and 825 (s) cm$^{-1}$

Example 25

Trans-4-(4-cyanophenyl)-1-n-hexyl-1-silacyclohexane GC-MS (70 eV) (m/z)$^+$: 145, 172, 229, 257 and 285

IR (liquid film) vmax: 2920 (s), 2227 (s), 2100 (s), 1608 (s), 1502 (m), 1458 (m), 1407 (m), 1184 (m), 987 (s), 889 (s), 879 (s) and 817 (s) cm$^{-1}$

Example 26

Trans-4-(4-cyanophenyl)-1-n-heptyl-1-silacyclohexane GC-MS (70 eV) (m/z)$^+$: 145, 200, 243, 271 and 298

IR (liquid film) vmax: 2920 (s), 2227 (s), 2100 (s), 1608 (s), 1502 (m), 1458 (m), 1408 (m), 1184 (m), 987 (s), 893 (s), 889 (s) and 820 (s) cm$^{-1}$

Example 27

Trans-4-(4-cyanophenyl)-1-n-nonyl-1-silacyclohexane $^{13}$C-NMR (67.5 MHz, CDCl$_3$): δ10.36 (s), 11.97 (s), 14.08 (s), 22.65 (s), 24.31 (s), 29.33 (s), 29.49 (s), 31.87 (s), 32.84 (s), 32.84 (s), 33.11 (s), 47.75 (s), 109.58 (s), 119.12 (s), 127.52 (s), 132.20 (s) and 153.99 (s) ppm IR (liquid film) vmax: 2916 (s), 2225 (m), 2090 (s), 1606 (m), 1502 (m), 1470 (m), 1406 (m), 989 (m), 933 (m), 889 (s) and 812 (s) cm$^{-1}$

Example 28

Trans-4-(4-iodophenyl)-1-n-propyl-1-silacyclohexane $^1$H-NMR (100 MHz, CDCl$_3$): δ0.40–2.55 (16H, m), 3.70–3.98 (1H, m), 6.80–7.01 (2H, m), 7.44–7.65 (2H, m) ppm IR (liquid film) vmax: 2920 (s), 2100 (s), 1480 (s), 1400 (s), 1060 (s), 1000 (s), 980 (s), 875 (s) and 810 (s) cm$^{-1}$

Example 29

Trans-4-(4-iodophenyl)-1-n-pentyl-1-silacyclohexane $^1$H-NMR (100 MHz, CDCl$_3$): δ0.40–1.02 (7H, m), 1.02–2.20 (12H, m), 2.36 (1H, tt), 3.70–3.95 (1H, m), 6.80–7.02 (2H, m), 7.44–7.66 (2H, m) ppm IR (liquid film) vmax: 2920 (s), 2100 (s), 1490 (s), 1410 (s), 1010 (s), 990 (s), 875 (s) and 810 (s) cm$^{-1}$

Example 30

Trans-4-(4-chloro-3-fluorophenyl)-1-n-propyl-1-silacyclohexane

Example 31

Preparation of trans-4-(4-(4-fluorophenyl)phenyl)-1-ethyl-1-silacyclohexane

Using the same method as Example 14, 23.2 g of 4-ethyl-4-p-tolyl-4-silacyclohexanone was reacted with 4-(4-fluorophenyl)phenyl magnesium bromide; the alcohol generated was treated with a dehydration reaction followed by catalytic reduction to obtain 4-(4-(4-fluorophenyl)phenyl)-1-ethyl-1-p-tolyl-1-silacyclohexane; this was then reacted with iodine monochloride; and then the product was reduced using lithium aluminum hydride to obtain 2.12 g (yield 71%) of the target product.

$^1$H-NMR (270 MHz, CDCl$_3$): δ0.64–0.81 (4H, m) 1.03–1.14 (5H, m), 1.82 (2H, ddd), 2.17–2.28 (2H, m), 2.48 (1H, tt), 3.84–3.94 (1H, m), 7.08–7.18 (2H, m), 7.25–7.35 (2H, m), 7.46–7.60 (4H, m) ppm IR (KBr disc) vmax: 2916 (s), 2096 (s), 1494 (s), 1238 (s), 966 (m), 887 (s), 881 (s) and 813 (s) cm$^{-1}$ The following compounds were obtained in the same manner as Example 31.

Example 32

Trans-4-(4-(4-fluorophenyl)phenyl)-1-n-pentyl-1-silacyclohexane $^{13}$C-NMR (67.5 MHz, CDCl$_3$): δ10.58 (s), 12.08 (s), 14.00 (s), 22.36 (s), 24.06 (s), 33.25 (s), 35.37 (s), 47.67 (s), 115.49 (s), 126.89 (s), 127.16 (s), 128.46 (d), 137.25 (d), 137.72 (s), 141.86 (s) and 162.27 (d) ppm IR (KBr disc) vmax: 2916 (s), 2096 (s), 1494 (s), 1238 (s), 982 (s), 883 (s), 835 (s) and 810 (s) cm$^{-1}$

Example 33

Trans-4-(4-(3, 4-difluorophenyl)phenyl)-1-n-propyl-1-silacyclohexane $^1$H-NMR (270 MHz, CDCl$_3$): δ0.60–0.74 (4H, m), 0.99 (3H, t), 1.00–1.12 (2H, m), 1.39–1.50 (2H, m), 1.73 (2H, ddd), 2.06–2.21 (2H, m), 2.44 (1H, tt), 3.80–3.90 (1H, m), 7.12–7.45 (7H, m) ppm IR (liquid film) vmax: 2918 (s), 2100 (s), 1529 (m), 1504 (s), 1403 (s), 1118 (m), 985 (m), 889 (s), 877 (s) and 812 (s) cm$^{-1}$

Example 34

Trans-4-(4-(3,4-difluorophenyl)phenyl)-1-n-pentyl-1-silacyclohexane $^1$H-NMR (270 MHz, CDCl$_3$): δ0.60–0.75 (4H, m), 0.90 (3H, t), 1.00–1.12 (2H, m), 1.25–1.46 (6H, m), 1.73 (2H, ddd), 2.07–2.21 (2H, m), 2.44 (1H, tt), 3.80–3.90 (1H, m), 7.12–7.46 (7H, m) ppm IR (KBr disc) vmax: 2916 (s), 2108 (s), 1605 (s), 1527 (s), 1506 (s), 1269 (s), 985 (s), 879 (s), 831 (s) and 812 (s) cm$^{-1}$

Example 35

Preparation of trans-4-(4-(4-fluorophenyl)phenyl)-1-n-propyl-1-silacyclohexane

A 15 ml tetrahydrofuran-toluene (1:1) solution of 1.0M 4-fluorophenyl zinc chloride was dripped into a mixture of 4.20 g of 4-(4-iodophenyl)-1-phenyl-1-n-propyl-1-silacyclohexane, 30 mg of tetrakis (triphenylphosphine) palladium(0) and 30 ml of tetrahydrofuran. After stirring for 8 hours at room temperature, the mixture was poured into a saturated aqueous solution of ammonium chloride and extraction was conducted using ethyl acetate. Using conventional washing, drying and concentration processes, 4-(4-(4-fluorophenyl)phenyl)-1-phenyl-1-n-propyl-1-silacyclohexane was obtained.

IR (KBr disc) νmax: 2910 (s), 1600 (m), 1500 (s), 1400 (m), 1225 (s), 1160 (m), 1110 (s), I1000 (m), 975 (m) and 880 (s) cm$^{-1}$ A 15 ml carbon tetrachloride solution of 1.0M iodine monochloride was added to this and the mixture was stirred for 30 minutes, followed by concentration. The concentrated residue was dissolved in 10 ml of tetrahydrofuran and then dripped into a mixture of 1.0 g of lithium aluminum hydride and 30 ml of tetrahydrofuran. The reaction mixture was stirred for 1 hour and then poured into 50 ml of 5% hydrochloric acid, followed by extraction using ethyl acetate. After conventional washing, drying and concentration procedures, purification was conducted by means of silica-gel chromatography to obtain 2.85 g (yield 91%) of the target product.

$^{13}$C-NMR (67.5 MHz, CDCl$_3$): δ10.60 (s), 14.67 (s), 17.79 (s), 17.90 (s), 33.25 (s), 47.26 (s), 115.49 (d), 126.88 (s), 127.16 (s), 128.46 (d), 137.25 (d), 137.72 (s), 147.86 (s) and 162.28 (d) ppm IR (liquid film) νmax: 2918 (s), 2086 (s), 1497 (s), 1238 (s), 1162 (m), 987 (s), 889 (s), 881(s) and 816 (s) cm$^{-1}$ The following compounds were obtained in the same manner as Example 35.

Example 36

Trans-4-(4-(4-trifluoromethoxyphenyl)phenyl)-1-n-pentyl-1-silacyclohexane $^{13}$C-NMR (67.5 MHz, CDCl$_3$): δ10.57 (s), 12.08 (s), 13.99 (s), 22.37 (s), 24.06 (s), 33.24 (s), 35.37 (s), 47.30 (s), 120.54 (q), 121.13 (s), 126.99 (s), 127.24 (s), 128.23 (s), 137.30 (s), 139.91 (s), 148.32 (s) and 148.42 (d) ppm IR (KBr disc) νmax: 2916 (s), 2092 (s), 1497 (s), 1263 (s), 1211 (s), 1163 (s), 987 (s), 890 (s), 881 (s) and 808 (s) cm$^{-1}$ Example 37

Trans-4-(4-(3,4-difluorophenyl)phenyl)-1-ethyl-1-silacyclohexane

We claim:

1. A silacyclohexanone compound represented by the following formula (I):

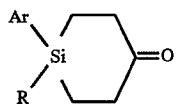
(I)

wherein Ar denotes a phenyl group or a tolyl group and R denotes a tolyl group, a linear-chain alkyl group with a carbon number of 2–10, a mono- or di-fluoroalkyl group with a carbon number of 1–10, a branched-chain alkyl group with a carbon number of 3–8 or an alkoxyalkyl group with a carbon number of 2–7.

2. A method of preparing a silacyclohexane liquid crystal compound comprising the steps of reacting a compound having the formula (I)

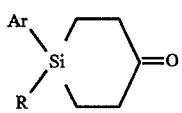
(I)

wherein Ar denotes a phenyl group or a tolyl group and R denotes a tolyl group, a linear-chain alkyl group with a carbon number of 2–10, a mono- or di-fluoroalkyl group with a carbon number of 1–10, a branched-chain alkyl group with a carbon number of 3–8 or an alkoxyalkyl group with a carbon number of 2–7, with an organometallic reagent represented by the following general formula

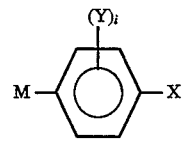

(in this formula, M denotes MgP (P denotes a halogen atom), ZnP or Li; X denotes a CN, F, Cl, Br, CF$_3$, OCF$_3$, OCHF$_2$, OCHFCl, OCF$_2$Cl, CF$_2$Cl, OCH$_2$CF$_2$H, R or OR group; Y denotes a halogen or CH$_3$; and i denotes an integer 0–2) to obtain a compound represented by the following general formula

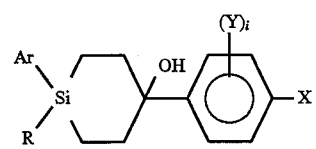

then conducting hydrogenolysis or dehydration followed by hydrogenation to obtain a compound represented by the following general formula

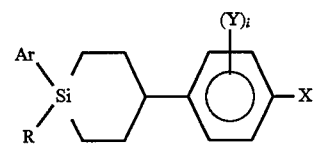

and finally conducting desilylation followed by reduction to obtain a silacyclohexane liquid crystal compound represented by the following general formula (II)

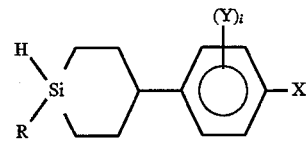
(II)

3. A method of preparing a silacyclohexane liquid crystal compound comprising the steps of reacting a compound having the formula (I)

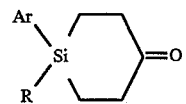
(I)

wherein Ar denotes a phenyl group or a tolyl group and R denotes a tolyl group, a linear-chain alkyl group with a carbon number of 2–10, a mono- or di-fluoroalkyl group with a carbon number of 1–10, a branched-chain alkyl group with a carbon number of 3–8 or an alkoxyalkyl group with a carbon number of 2–7, with an organometallic reagent represented by the following general formula

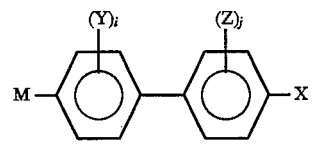

(in this formula, M denotes MgP (P denotes a halogen atom), ZnP or Li; X denotes a CN, F, Cl, Br, CF$_3$, OCF$_3$, OCHF$_2$, OCHFCl, OCF$_2$Cl, CF$_2$Cl, OCH$_2$CF$_2$H, R or OR group; Y and Z denote a halogen or CH$_3$; i and j both denote integers 0–2) to obtain a compound represented by the following general formula

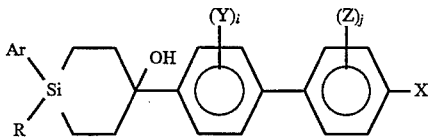

then conducting hydrogenolysis or dehydration followed by hydrogenation to obtain a compound represented by the following general formula

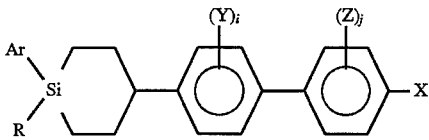

and finally conducting desilylation followed by reduction to obtain a silacyclohexane liquid crystal compound represented by the following general formula (III)

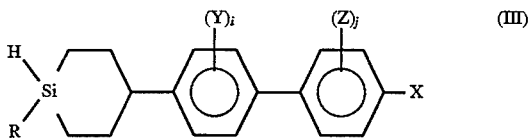

4. A method of preparing a silacyclohexane liquid crystal compound comprising the steps of reacting a compound having the formula (I)

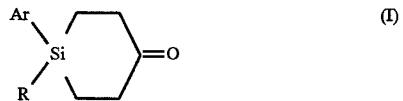

wherein Ar denotes a phenyl group or a tolyl group and R denotes a tolyl group, a linear-chain alkyl group with a carbon number of 2–10, a mono- or di-fluoroalkyl group with a carbon number of 1–10, a branched-chain alkyl group with a carbon number of 3–8 or an alkoxyalkyl group with a carbon number of 2–7, with an organometallic reagent represented by the following general formula

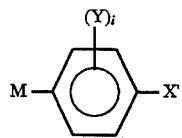

(in this formula, M denotes MgP (P denotes a halogen atom), ZnP or Li; X' denotes a halogen; Y denotes a halogen or CH$_3$; i denotes an integer 0–2) to obtain a compound represented by the following general formula

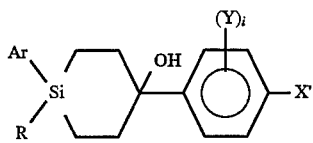

then conducting hydrogenolysis or dehydration followed by hydrogenation to obtain a compound represented by the following general formula

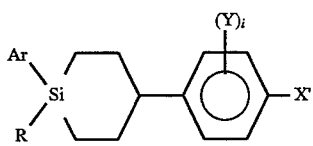

then reacting this compound with an organometallic reagent represented by the following general formula

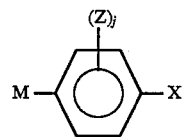

(X denotes a CN, F, Cl, Br, CF$_3$, OCF$_3$, OCHF$_2$, OCHFCl, OCF$_2$Cl, CF$_2$Cl, OCH$_2$CF$_2$H, R or OR group; Z denotes a halogen or CH$_3$; j denotes an integer 0–2) in the presence of a transition metal catalyst to obtain a compound represented by the following general formula

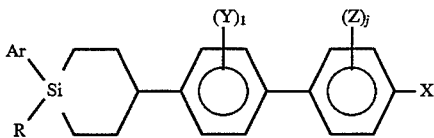

and finally conducting desilylation followed by reduction to obtain a silacyclohexane liquid crystal compound represented by the following general formula (III)

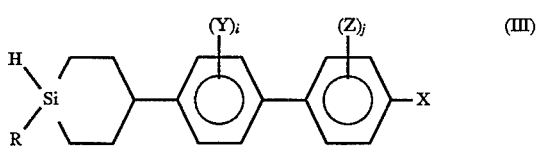

* * * * *